United States Patent
Gross

(10) Patent No.: US 9,872,817 B2
(45) Date of Patent: Jan. 23, 2018

(54) ALKALIZING DELIVERY SYSTEM FOR PROMOTING AN OPTIMAL ORAL SALIVARY PH

(71) Applicant: Lewis H. Gross, New York, NY (US)

(72) Inventor: Lewis H. Gross, New York, NY (US)

( * ) Notice: Subject to any disclaimer, the term of this patent is extended or adjusted under 35 U.S.C. 154(b) by 0 days.

(21) Appl. No.: 15/378,973

(22) Filed: Dec. 14, 2016

(65) Prior Publication Data

US 2017/0367938 A1   Dec. 28, 2017

Related U.S. Application Data

(63) Continuation-in-part of application No. 15/191,736, filed on Jun. 24, 2016.

(51) Int. Cl.
| | |
|---|---|
| A61K 8/02 | (2006.01) |
| A61K 8/36 | (2006.01) |
| A61K 8/92 | (2006.01) |
| A61K 8/97 | (2017.01) |
| A61Q 11/00 | (2006.01) |
| B08B 1/00 | (2006.01) |
| A61K 8/19 | (2006.01) |

(52) U.S. Cl.
CPC .............. *A61K 8/19* (2013.01); *A61K 8/0216* (2013.01); *A61K 8/922* (2013.01); *A61K 8/97* (2013.01); *A61Q 11/00* (2013.01); *B08B 1/002* (2013.01); *A61K 2800/92* (2013.01)

(58) Field of Classification Search
CPC ... A61K 8/02; A61K 8/36; A61K 8/92; A61K 8/97; A61Q 11/00; B08B 1/00
See application file for complete search history.

(56) References Cited

FOREIGN PATENT DOCUMENTS

WO    WO 2016/105439    *   6/2016    ............... A61K 8/31

* cited by examiner

*Primary Examiner* — Brian P Mruk
(74) *Attorney, Agent, or Firm* — Dunlap Bennett & Ludwig PLLC

(57) ABSTRACT

An alkalizing delivery system for promoting healthier saliva is provided. The alkalizing delivery system may take many portable forms that include a saliva buffering agent and a saliva alkali agent adapted to transiently change the pH balance of a user's saliva without the use of self-foaming agents.

17 Claims, 1 Drawing Sheet

ALKALIZING DELIVERY SYSTEM FOR PROMOTING AN OPTIMAL ORAL SALIVARY PH

CROSS-REFERENCE TO RELATED APPLICATION

This application is a continuation-in-part of U.S. nonprovisional application Ser. No. 15/191,736, filed Jun. 24, 2016, the contents of which are herein incorporated by reference.

BACKGROUND OF THE INVENTION

The present invention relates to dental hygiene and, more particularly, to an alkalizing delivery system for promoting dental hygiene through transiently changing the pH balance of oral salivary acidity for maintaining optimal range thereof.

Dental caries, also known as tooth decay, cavities, or caries, is a breakdown of teeth due to activities of bacteria. This occurs due to acid made from food debris or sugar on the tooth surface, usually in the form of biofilm. If this biofilm is left in contact with the tooth, these acids may cause demineralization, dissolving its mineral content. The process can, however, be reversed through remineralization if the acid is neutralized by saliva.

Therefore, oral saliva plays an important role in digestion and may be an indication of over-all systematic health. Alkaline saliva (pH 7.2 or higher) allows teeth to remineralize, thereby preventing and sometimes curing caries, while acidic saliva causes cervical root erosion and sensitivity.

As a corollary, oral saliva acidity is detrimental to oral health, leading to cavities and periodontal disease, and is systematic health as well.

Presently, salivary acidity is treated with fluoride, abrasives and/or chemicals. Such current treatments, however, treat symptoms rather than adjust salivary conditions, and do not promote healthier saliva.

As can be seen, there is a need for an alkalizing delivery system for promoting dental hygiene through transiently changing the pH balance of oral salivary acidity for maintaining optimal range thereof.

SUMMARY OF THE INVENTION

In one aspect of the present invention, an alkalizing composition for promoting an optimal pH balance of saliva when applied in the mouth, including approximately 0.04% by weight of a saliva buffering agent; and an effective amount of a saliva anti-acid agent.

In another aspect of the present invention, an alkalizing delivery system includes an alkalizing composition for promoting an optimal pH balance of saliva when applied in the mouth, including approximately 0.04% by weight of a coconut oil; approximately 0.06% by weight of turmeric; approximately 79 to 80% by weight of sodium bicarbonate; and an effective amount of plaque and stain removing agents selected from the group consisting of tea tree oil and ginger extract.

In yet another aspect of the present invention, a method of transiently changing the pH balance of saliva acidity for promoting dental hygiene, including the steps of: providing a tablet forming an alkalizing slurry when placed in water, wherein the alkalizing slurry includes having approximately 0.04% by weight of a coconut oil, approximately 0.006% by weight of turmeric, and effective amount of saliva anti-acid agent; and applying the alkalizing slurry to the mouth.

These and other features, aspects, and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an alkalizing delivery system for promoting healthier saliva. The alkalizing delivery system may take many portable forms that include a saliva buffering agent and a saliva alkali agent adapted to transiently changing the pH balance of a user's saliva without the use of self-foaming agents.

Figure 1:
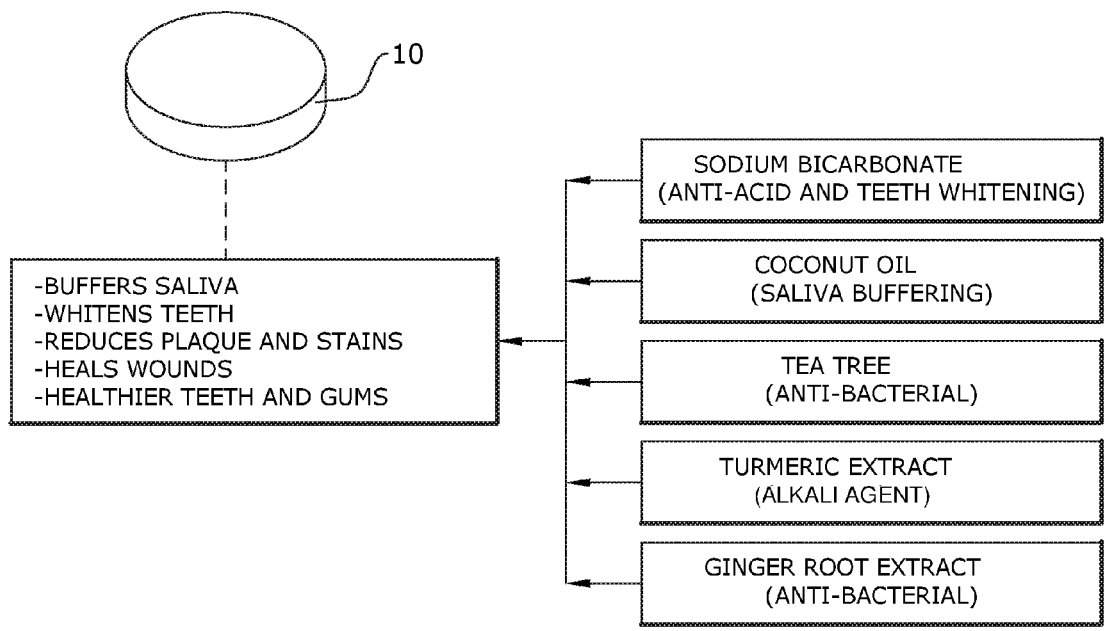
FIG. 1 is a flow chart of an exemplary embodiment of the present invention.

Referring to FIG. 1, the present invention may include an alkalizing delivery system for promoting healthier saliva through transiently changing the pH balance of salivary acidity. The alkalizing delivery system may include the following alkalizing compositions:

Embodiment 1

(a) a saliva anti-acid and teeth whitening agent;
(b) a saliva buffering agent;
(c) an alkali agent
(d) plaque and stain removing agents; and in certain embodiments
(e) healing agents.

Embodiment 2

(a) saliva anti-acid and teeth whitening agent;
(b) a sugar-free sweetener (optional);
(c) saliva buffering agent;
(d) an alkali agent; and
(e) plaque and stain removing and healing agents.

Embodiment 3

(a) saliva anti-acid and teeth whitening agent;
(b) a sugar-free sweetener;
(c) saliva buffering agent; and
(d) plaque and stain removing and healing agents.

The anti-acid and teeth whitening agent may be sodium bicarbonate.

The saliva buffering may be coconut oil.

The alkali agent may be turmeric. The alkali agent and saliva buffering agent may be adapted to providing alkalizing of a user's saliva without self-foaming agents, which are unhealthy.

The plaque and stain removing agents may be selected from the group consisting of tea tree oil, ginger root extract, and/or peppermint oil.

The healing agents may be essential oils. In some embodiment, the plaque and stain removing agents may be the same as the healing agents, or in other words the plaque and stain removing agents may contribute to the healing process.

The sugar-free sweetener may be xylitol or other compound adapted to prevent tooth decay and dry mouth.

The alkalizing delivery system may have the following alkalizing compositions:

Embodiment 1

(i) 900 mg saliva anti-acid and teeth whitening agent;
(ii) 50 mg saliva buffering agent;
(iii) 10 mg saliva alkali agent; and
(iv) 6 to 18 mg plaque and stain removing and healing agents.

Embodiment 2a (i) 1100 mg saliva anti-acid and teeth whitening agent;
(ii) 70 mg sugar-free sweetener (optional);
(iii) 60 mg saliva buffering agent;
(iv) 10 mg saliva alkali agent; and
(v) 6 to 18 mg plaque and stain removing and healing agents.

Embodiment 2b (vi) 1300 mg saliva anti-acid and teeth whitening agent;
(vii) 250 mg sugar-free sweetener (optional);
(viii) 60 mg saliva buffering agent;
(ix) 10 mg saliva alkali agent; and
(x) 2 to 22 mg plaque and stain removing and healing agents.

Embodiment 3a (i) 1200 mg saliva anti-acid and teeth whitening agent;
(ii) 70 mg sugar-free sweetener (optional);
(iii) 60 mg saliva buffering agent; and
(iv) 12 mg plaque and stain removing and healing agents.

Embodiment 3b (v) 1300 mg saliva anti-acid and teeth whitening agent;
(vi) 250 mg sugar-free sweetener (optional);
(vii) 60 mg saliva buffering agent; and
(viii) 2 to 15 mg plaque and stain removing and healing agents.

The saliva anti-acid, saliva buffering agent and alkali agent may be adapted to transiently change the pH balance of a user's saliva.

The plaque and stain removing and healing agents may include 12 mg of tea tree oil and 6 mg of ginger root extract. In embodiment 2b, the plaque and stain removing and healing agents may include 12.5 mg of tea tree oil, 7 mg of ginger root extract, and/or 2.5 mg of peppermint oil. In embodiment 3b, the plaque and stain removing and healing agents may include 12.5 mg of tea tree oil and/or 2.5 mg of peppermint oil.

The alkalizing delivery system may take the form of a mouthwash, slurry, paste, tablet 10 or the like. The tablet 10 form may be adapted to be effervescent and include essential oils and spices, and adapted so that the alkalizing delivery system dissolves properly and does not go rancid.

Figure 2:
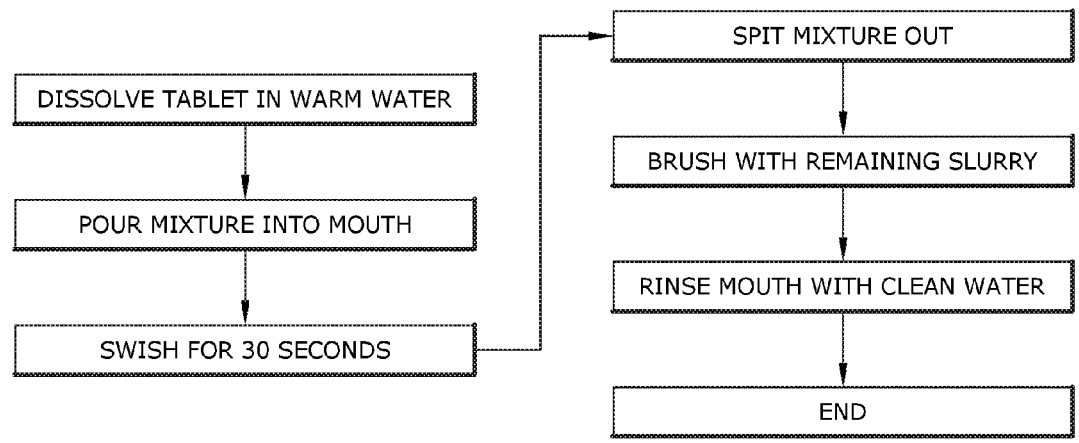
FIG. 2 is a flow chart of an exemplary embodiment of the present invention.

Referring to FIG. 2, a method of using the present invention may include the following. The alkalizing delivery system disclosed above may be provided in tablet 10 form. A user may dissolve the tablet 10 in warm water, and the resulting mixture may be swished in their mouth for approximately 30 seconds or a sufficient time. Then the user may spit the resulting mixture out before brushing with remaining residual slurry. Thereafter, the user may rinse their mouth with clean water.

Furthermore, the tablet can be broken into smaller quantity and taken directly into mouth and diluted with water. Moreover, the tablet 10 may form an alkalizing slurry when placed in water, wherein the alkalizing slurry includes the predetermine embodiment of alkalizing composition. The tablet 10 can be self-dissolving in the mouth of a user.

By regularly using the alkalizing delivery system, no matter what the form, the user would transiently change the pH balance of their salivary acidity, promoting healthier teeth and gums as the alkaline saliva allows for remineralization and anti-bacterial effects.

The tablet form enables a pill that when put in a water solution creates a toothpaste and/or a mouthwash that is used for anti-caries, wherein the main ingredient of the alkalizing composition is sodium bicarbonate and coconut oil, and wherein the alkalizing composition may or may not contain fluoride and/or self-foaming agents.

Furthermore, the alkalizing delivery system is portable, does not contain any chemicals, and is Vegan and gluten free. The alkalizing composition can in effect be a dry (non-dissolved/hydrated tablet) portable mouthwash and/or toothpaste ideal for military, prisons, air travel and the like.

It should be understood, of course, that the foregoing relates to exemplary embodiments of the invention and that modifications may be made without departing from the spirit and scope of the invention as set forth in the following claims.

What is claimed is:

1. An alkalizing composition for promoting an optimal pH balance of saliva when applied in the mouth, comprising:
   (a) approximately 0.04% by weight of a saliva buffering agent; and
   (b) approximately 79 to 80% by weight of a saliva anti-acid agent.

2. The alkalizing composition of claim 1, further comprising approximately 0.01% by weight of an alkali agent.

3. The alkalizing composition of claim 1, further comprising an effective amount of plaque and stain removing agents.

4. The alkalizing composition of claim 1, wherein the saliva buffering agent includes a coconut oil.

5. The alkalizing composition of claim 1, wherein the saliva anti-acid agent buffering agent includes sodium bicarbonate.

6. The alkalizing composition of claim 3, wherein the plaque and stain removing agents is selected from the group consisting of tea tree oil and ginger extract.

7. The alkalizing composition of claim 1, further comprising a tablet forming an alkalizing slurry when placed in water, wherein the alkalizing slurry includes the alkalizing composition.

8. The alkalizing composition of claim 7, wherein the tablet dissolves into the alkalizing slurry directly in the mouth.

9. An alkalizing composition for promoting an optimal pH balance of saliva when applied in the mouth, comprising:

(a) approximately 0.04% by weight of a coconut oil;
(b) approximately 0.01% by weight of an alkali agent, wherein the alkali agent includes turmeric; and
(c) approximately 79-80% by weight of sodium bicarbonate.

10. The alkalizing composition of claim 9, further comprising a tablet forming an alkalizing slurry when placed in water, wherein the alkalizing slurry includes the alkalizing composition.

11. The alkalizing composition of claim 10, wherein the tablet dissolves into the alkalizing slurry directly in the mouth.

12. A method of transiently changing the pH balance of saliva acidity for promoting dental hygiene, comprising the steps of:
providing a tablet forming an alkalizing slurry when placed in water, wherein the alkalizing slurry includes having approximately 0.04% by weight of a coconut oil, approximately 0.006% by weight of turmeric, and effective amount of saliva anti-acid agent; and
applying the alkalizing slurry to the mouth.

13. The method of claim 12, further comprising the step of initially dissolving the tablet in water before applying to the mouth.

14. The method of claim 12, further comprising the step of dissolving the tablet in the mouth.

15. The method of claim 12, further comprising the step of brushing the alkalizing slurry when in the mouth.

16. The alkalizing composition of claim 9, further comprising an effective amount of plaque and stain removing agents.

17. The alkalizing composition of claim 9, further comprising an effective amount of plaque and stain removing agents selected from the group consisting of tea tree oil and ginger extract.

* * * * *